United States Patent
Lane et al.

(10) Patent No.: US 9,539,441 B2
(45) Date of Patent: Jan. 10, 2017

(54) RADIOTHERAPY SYSTEM WITH ADVANCED GRAPHICAL USER INTERFACE

(71) Applicant: Elekta AB (Publ), Stockholm (SE)

(72) Inventors: Derek Graham Lane, San Mateo, CA (US); Andrew Philip Long, Leatherhead (GB)

(73) Assignee: ELEKTA AB (PUBL), Stockholm (SE)

(*) Notice: Subject to any disclaimer, the term of this patent is extended or adjusted under 35 U.S.C. 154(b) by 264 days.

(21) Appl. No.: 14/275,837

(22) Filed: May 12, 2014

(65) Prior Publication Data
US 2015/0082220 A1 Mar. 19, 2015

Related U.S. Application Data

(60) Provisional application No. 61/877,608, filed on Sep. 13, 2013.

(51) Int. Cl.
| | |
|---|---|
| *G06F 3/048* | (2013.01) |
| *A61N 5/10* | (2006.01) |
| *G06F 3/0481* | (2013.01) |
| *G06F 3/0482* | (2013.01) |
| *G06F 3/0484* | (2013.01) |

(52) U.S. Cl.
CPC .............. *A61N 5/1039* (2013.01); *A61N 5/103* (2013.01); *G06F 3/0482* (2013.01); *G06F 3/04817* (2013.01); *G06F 3/04842* (2013.01); *A61N 5/1048* (2013.01); *A61N 2005/1074* (2013.01)

(58) Field of Classification Search
CPC ............................ G06F 3/0481–3/0485; G06F 17/3002–17/30864; G06F 19/26
See application file for complete search history.

(56) References Cited

U.S. PATENT DOCUMENTS

| | | | | |
|---|---|---|---|---|
| 6,049,622 | A * | 4/2000 | Robb | G06T 19/003 382/128 |
| 2004/0125121 | A1* | 7/2004 | Pea | G11B 27/105 715/716 |
| 2007/0189737 | A1* | 8/2007 | Chaudhri | G06F 3/0482 386/234 |
| 2009/0262894 | A1* | 10/2009 | Shukla | A61N 5/1049 378/65 |
| 2014/0161339 | A1* | 6/2014 | Wakai | G06T 7/0012 382/131 |

FOREIGN PATENT DOCUMENTS

| | | |
|---|---|---|
| WO | WO 2009/061475 A2 | 5/2009 |
| WO | WO 2013/039018 A1 | 3/2013 |
| WO | WO 2013/108139 A2 | 7/2013 |

OTHER PUBLICATIONS

International Search Report and Written Opinion dated Nov. 27, 2014 in corresponding International Application No. PCT/IB2014/064446, 13 pages.

* cited by examiner

*Primary Examiner* — Claudia Dragoescu
(74) *Attorney, Agent, or Firm* — Finnegan, Henderson, Farabow, Garrett & Dunner, LLP

(57) ABSTRACT

The present disclosure relates to methods of systems for radiotherapy. Embodiments of the present disclosure may provide a carousel to display the plurality of images to a user and receive an input from the user for selecting one or more images displayed in the carousel. A graphical user interface may be provided for displaying to the user the one or more images selected from the carousel.

17 Claims, 13 Drawing Sheets

| Status | Date/Time | Associ... | Association Name | Type | Sup | Lat | Ant | Imager | Proj. | Cp | Fld | Blk | Oth | Img | Off |
|---|---|---|---|---|---|---|---|---|---|---|---|---|---|---|---|
| ⊞ Kiesel, Allen / 456753 (image count=2), (Oldest date: 2/5/2009 1:53 PM) | | | | | | | | | | | | | | | |
| ⊞ Lonsford, Larry / 90008 (Image count=2), (Oldest date: 4/20/2009 1:36 PM) | | | | | | | | | | | | | | | |
| ⊞ LungSBRT, Test / LungSBRT (Image count=7), (Oldest date: 9/13/2009 12:29 PM) | | | | | | | | | | | | | | | |
| ⊞ MacDonald, Pat / 90009 (Image count=1), (Oldest date: 4/28/2009 10:32 AM) | | | | | | | | | | | | | | | |
| ⊟ Prostate, Test / Prostate (Image count=10), (Oldest date: 8/20/2008 2:18 PM) | | | | | | | | | | | | | | | |
| | 8/21/2008 4:53 PM | Site | Prostate | CBCT | Inf 7.0 cm | Lft 20.2 cm | Pos 20.2 cm | | | | | | | Yes | |
| | 8/22/2008 4:52 PM | Site | Prostate | CBCT | Inf 7.0 cm | Lft 20.4 cm | Pos 19.8 cm | | | | | | | Yes | |
| | 8/25/2008 5:01 PM | Site | Prostate | CBCT | Inf 6.8 cm | Lft 20.7 cm | Pos 19.8 cm | | | | | | | Yes | |
| | 8/26/2008 5:07 PM | Site | Prostate | CBCT | Inf 6.8 cm | Lft 20.8 cm | Pos 19.2 cm | | | | | | | Yes | |
| | 8/27/2008 5:13 PM | Site | Prostate | CBCT | Inf 6.8 cm | Lft 20.2 cm | Pos 19.5 cm | | | | | | | Yes | |
| | 8/28/2008 5:16 PM | Site | Prostate | CBCT | Inf 6.6 cm | Lft 20.4 cm | Pos 19.5 cm | | | | | | | Yes | |
| | 8/29/2008 5:19 PM | Site | Prostate | CBCT | Inf 6.8 cm | Lft 20.7 cm | Pos 20.0 cm | | | | | | | Yes | |
| | 9/1/2008 5:23 PM | Site | Prostate | CBCT | Inf 6.5 cm | Lft 20.5 cm | Pos 20.0 cm | | | | | | | Yes | |
| | 9/2/2008 5:28 PM | Site | Prostate | CBCT | Inf 6.7 cm | Lft 20.7 cm | Pos 19.6 cm | | | | | | | Yes | |
| | 8/20/2008 2:18 PM | | | CT | | | | | | | | | | | |

Fig. 1

| Images – All Images (All) | | | | | | | | | | |
|---|---|---|---|---|---|---|---|---|---|---|
| ▽ Filters ⇪ Open ⧉ Close All ☑ Review ⊟ Review List ⊡ Export ⎙ Print ✕ Delete ⊛ SRO Browser ⟳ Refresh | | | | | | | | | | |
| Date/Time | Associ... | Association Name | Type | Sup | Lat | Ant | Imager | Proj. | Cp | Fld | Blk |
| 8/20/2008 2:18 PM | | | CT | | | | | | | | |
| 8/21/2008 4:53 PM | Site | Prostate | CBCT | Inf 1.0 cm | Lft 0.0 cm | Ant 0.4 cm | | | | | |
| 8/22/2008 4:52 PM | Site | Prostate | CBCT | Inf 1.0 cm | Lft 0.1 cm | Ant 0.7 cm | | | | | |
| 8/25/2008 5:01 PM | Site | Prostate | CBCT | Inf 0.7 cm | Lft 0.3 cm | Ant 0.7 cm | | | | | |
| 8/26/2008 5:07 PM | Site | Prostate | CBCT | Inf 0.5 cm | Lft 0.3 cm | Ant 1.0 cm | | | | | |
| 8/27/2008 5:13 PM | Site | Prostate | CBCT | Inf 0.9 cm | Lft 0.1 cm | Ant 0.8 cm | | | | | |
| 8/28/2008 5:16 PM | Site | Prostate | CBCT | Inf 0.7 cm | Lft 0.0 cm | Ant 0.8 cm | | | | | |
| 8/29/2008 5:19 PM | Site | Prostate | CBCT | Inf 0.7 cm | Lft 0.3 cm | Ant 0.4 cm | | | | | |
| 9/1/2008 5:23 PM | Site | Prostate | CBCT | Inf 0.6 cm | Lft 0.2 cm | Ant 0.5 cm | | | | | |
| 9/2/2008 5:28 PM | Site | Prostate | CBCT | Inf 0.7 cm | Lft 0.3 cm | Ant 0.9 cm | | | | | |
| 2/15/2008 10:01 AM | | | MR | | | | | | | | |
| 1/31/2013 4:50 PM | | | RPOa | DRR | | | | | 208.0 | | |
| 1/31/2013 4:50 PM | | | RPO2a | DRR | | | | | 260.0 | | |
| 1/31/2013 4:50 PM | | | RAOa | DRR | | | | | 312.0 | | |
| 1/31/2013 4:50 PM | | | APa | DRR | | | | | 0.0 | | |
| 1/31/2013 4:50 PM | | | LAOa | DRR | | | | | 52.0 | | |
| 1/31/2013 4:50 PM | | | LPOa | DRR | | | | | 104.0 | | |
| 1/31/2013 4:50 PM | | | LPO2a | DRR | | | | | 156.0 | | |
| 1/31/2013 4:50 PM | | | RPO | DRR | | | | | 208.0 | | |
| 1/31/2013 4:50 PM | | | RPO2 | DRR | | | | | 260.0 | | |
| 1/31/2013 4:51 PM | | | RAO | DRR | | | | | 312.0 | | |
| 1/31/2013 4:51 PM | | | AP | DRR | | | | | 0.0 | | |
| 1/31/2013 4:51 PM | | | LAO | DRR | | | | | 52.0 | | |

Fig. 2

Localization Trend Review (Beam) – MR#: Prostate  Prostate, Test

Course: 75 — 302
Site Name: Prostate — 304
Patient Orientation: Head In, Supine

Status: Inactive
Source:

☐ Exclude

[OK] [Cancel]

Site / Image List

| Sts | Description |
|-----|-------------|
| | ⊟ Prostate |
| | └ 3D |
| | └ 3D |
| | └ 3D |
| | └ 3D |
| | └ 3D |
| | └ 3D |
| | └ 3D |
| | └ 3D |
| | └ Site 1 |

306

| Date | Time | Superior | | Lateral | | Anterior | | Coronal | | Sagittal | | Transverse | | Mag. |
|------|------|----------|---|---------|---|----------|---|---------|---|---------|---|-----------|---|------|
| | | S/I | cm | L/R | cm | A/P | cm | Dir. | deg. | Dir. | deg. | Dir. | deg. | |
| 8/21/2008 | 4:53 PM | Inf | 1.0 | Lft | 0.1 | Ant | 0.4 | CW | 0.6 | CW | 1.6 | CW | 0.8 | 1.1 |
| 8/22/2008 | 4:52 PM | Inf | 1.0 | Lft | 0.1 | Ant | 0.7 | CW | 0.4 | CW | 2.4 | CW | 1.4 | 1.2 |
| 8/25/2008 | 5:01 PM | Inf | 0.7 | Lft | 0.3 | Ant | 0.7 | CW | 0.2 | CW | 1.8 | CW | 0.6 | 1.0 |
| 8/26/2008 | 5:07 PM | Inf | 0.5 | Lft | 0.1 | Ant | 1.0 | CW | 0.2 | CW | 2.5 | CW | 0.7 | 1.2 |
| 8/27/2008 | 5:13 PM | Inf | 0.9 | Lft | 0.1 | Ant | 0.8 | CW | 0.1 | CW | 3.9 | CW | 0.9 | 1.2 |
| 8/28/2008 | 5:16 PM | Inf | 0.7 | Lft | 0.0 | Ant | 0.8 | CCW | 0.4 | CW | 1.7 | CW | 0.0 | 1.1 |
| 8/29/2008 | 5:19 PM | Inf | 0.7 | Lft | 0.3 | Ant | 0.4 | CCW | 0.5 | CW | 0.1 | CW | 0.5 | 0.9 |
| 9/01/2008 | 5:23 PM | Inf | 0.6 | Lft | 0.2 | Ant | 0.5 | CCW | 0.6 | CW | 3.0 | CW | 0.4 | 0.8 |
| 9/02/2008 | 5:28 PM | Inf | 0.7 | Lft | 0.3 | Ant | 0.9 | CCW | 0.9 | CW | 2.3 | CW | 0.6 | 1.2 |

308 — 310 — 312 — 314

Localization Offset (Beam)

[Derive Localization Offset]

| | Current (cm) | Additional (cm) | | New (cm) |
|---|---|---|---|---|
| Superior/Inferior: | 0.0 | Superior ▼ | 0.0 | Superior 0.0 |
| Right/Left: | 0.0 | Left ▼ | 0.0 | Left 0.0 |
| Anterior/Posterior: | 0.0 | Anterior ▼ | 0.0 | Anterior 0.0 |

316

[Graphs] — 318

RADIOTHERAPY SYSTEM WITH ADVANCED GRAPHICAL USER INTERFACE

CROSS REFERENCE TO RELATED APPLICATION(S)

This application claims the benefit of priority to U.S. Provisional Application No. 61/877,608, filed on Sep. 13, 2013, the entire content of which has been incorporated herein by reference.

TECHNICAL FIELD

This disclosure relates generally to radiation therapy (radiotherapy) system. More specifically, it is related to a radiotherapy system having an advanced graphical user interface (GUI) for displaying and/or manipulating medical images.

BACKGROUND

Radiation therapy has been utilized to treat tumors in mammalian (e.g., human and animal) tissue. In a radiation therapy treatment session, a high energy beam is applied from an external source towards a patient to produce a collimated beam of radiation directed to a target site of a patient. The placement and dose of the radiation beam must be accurately controlled to ensure that the tumor receives sufficient radiation, and on the other hand, to minimize damage to the surrounding healthy tissue.

One way to improve the accuracy of the beam placement is through image guided radiation therapy process, in which a series of patent images are obtained to aid the application of radiation beams. Physicians can use the patient images to identify a target region (e.g., the tumor) and to identify critical organs near the tumor. They then manually segment the tumor that is to receive a prescribed radiation dose and further segment the critical organs that are at risk of damage from the radiation treatment. Finally, a treatment plan can be created using an optimization technique based on the segmentation of the tumor and the critical organs.

However, reviewing large amount of patent images is a daunting challenge faced by radiation oncologists. For example, a typical radiation oncologist normally reviews images for 20 patients daily. If cone beam CT (CBCT) images are used, the amount of data to be reviewed can exceed 2 GB per day.

The review burden can be lessened by considering that typically greater than 90% of IGRT images reveal no unusual changes, and each image can be quickly assessed before moving on to the next image. Therefore, it would be useful to develop an efficient way to quickly identify the minority of images that warrant a more thorough review.

SUMMARY

Certain embodiments of the present disclosure relate to a radiotherapy apparatus. The radiotherapy apparatus may comprise a memory for storing a plurality of images and a processor communicatively coupled to the memory. The processor may be configured to execute instructions for providing a carousel to display the plurality of images to a user. The processor may also be configured to execute instructions for receiving an input from the user for selecting one or more images displayed in the carousel. In addition, the processor may be configured to execute instructions for generate a graphical user interface configured for displaying to the user the one or more images selected from the carousel.

Certain embodiments of the present disclosure relate to a method for treating a patient with a radiotherapy device. The method may comprise storing a plurality of images of one or more patients in a memory and selecting a group of images from the stored plurality of images stored in the memory. The method may also comprise loading a carousel with thumbnail images of the selected group of images and displaying the thumbnails images in chronological order in the carousel. In addition, the method may comprise receiving a user selection of at least one thumbnail image from the carousel and correlating the selection of the thumbnail image to a corresponding image stored in the memory. Moreover, the method may comprise displaying the correlated image stored in the memory on a user selected area in a user-interface.

Additional objects and advantages of the present disclosure will be set forth in part in the following detailed description, and in part will be obvious from the description, or may be learned by practice of the present disclosure. The objects and advantages of the present disclosure will be realized and attained by means of the elements and combinations particularly pointed out in the appended claims.

It is to be understood that the foregoing general description and the following detailed description are exemplary and explanatory only, and are not restrictive of the invention, as claimed.

BRIEF DESCRIPTION OF THE DRAWINGS

The accompanying drawings, which constitute a part of this specification, illustrate several embodiments and, together with the description, serve to explain the disclosed principles.

FIG. 1 illustrates an exemplary image work list, according to some embodiments of the present disclosure.

FIG. 2 illustrates an exemplary image list for a patient, according to some embodiments of the present disclosure.

FIG. 3 illustrates an exemplary trend table, according to some embodiments of the present disclosure.

DETAILED DESCRIPTION

Figure 4:
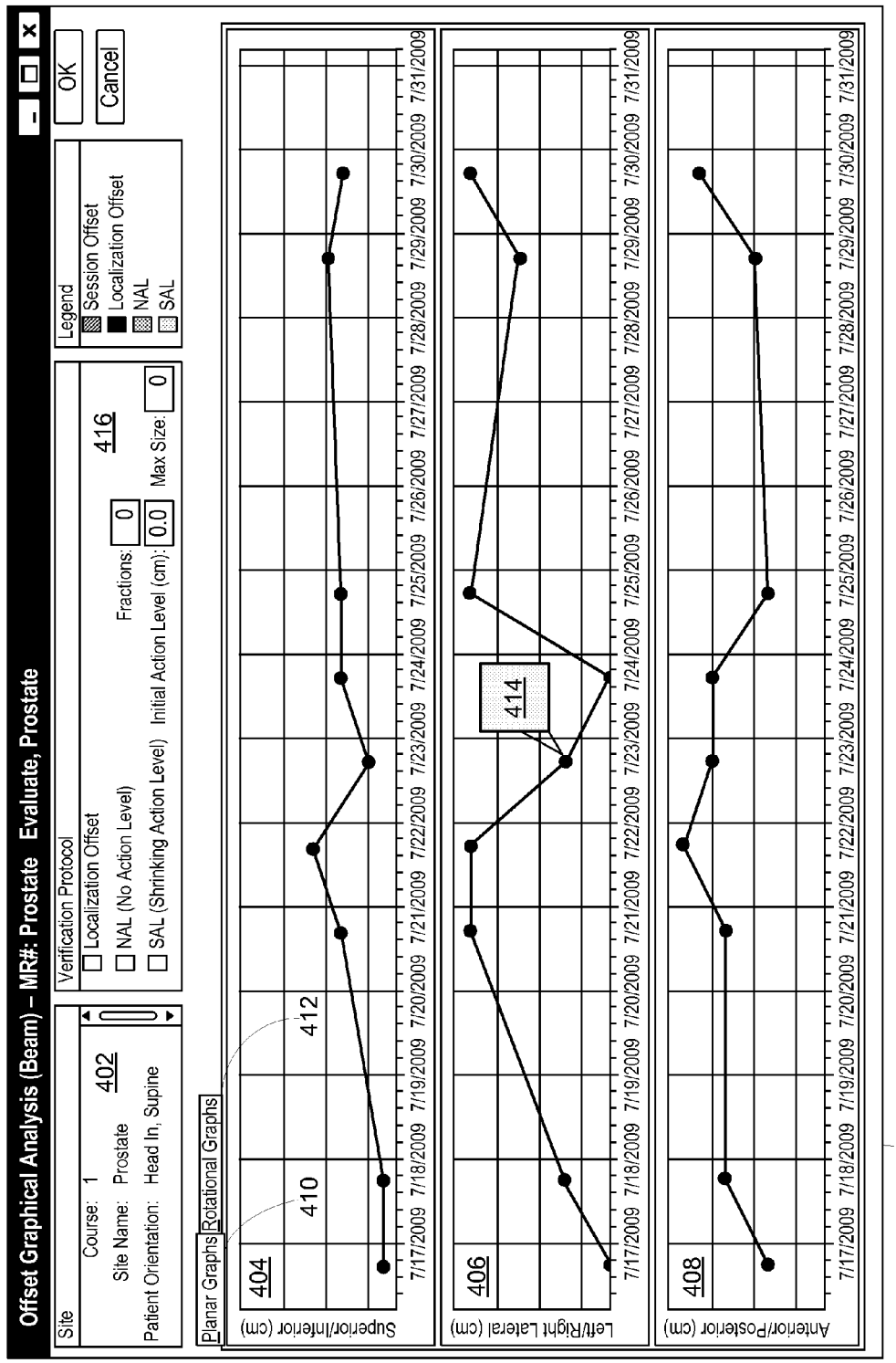
FIG. 4 illustrates an exemplary graphical representation of offset trends, according to some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Embodiments of the present disclosure may include a radiotherapy system. The radiotherapy system may include a high-energy beam source and a control center to control radiation application. To guide beam placement, a plurality of images of a patient can be obtained through one or more different image acquisition methods. For example, the patient images may include Computed Tomography (CT) images, x-ray images (e.g., fluoroscopic x-ray image sequences), radiotherapy portal images, stereo pairs of portal images, stereo pairs of x-ray images, Magnetic Resonance Imaging (MRI) images, Positron Emission Tomography (PET) images, Single-Photon Emission Computed Tomography (SPECT) images, ultrasound images, or other suitable medical images. These images may be stored in a memory (e.g., the memory may be local to the radiation therapy system or may be remote).

The image data may be managed by an oncology information system (OIS). In some embodiments, a QIS may use a tabular format to store new and existing data. In other words, data may be stored in a set of tables. The tables may include text-based columns for storing and/or conveying numerous pieces of data, including, for example, image comments and notes, approval status, numerical offset values, and change orders. The tables may appear in multiple contexts.

From the tabular view of data, a physician may review images using separately launched viewers for, for example, cone beam CT (CBCT) or portal images and their associated reference images. These image viewers may be designed to enable a physician to review a single image at a time. When review of that image is completed, the viewer may be dismissed. Image review and localization of trend review using such image viewers may be time consuming.

For example, in image review, a physician may inspect one or more localization images acquired during the treatment process of a patient, and may assign an approval status to the image(s) (e.g., Approve/Reject/Request-Repeat, and the like) based on criteria such as the quality of the image itself and/or the outcome of image registration operations performed using the image.

In localization trend review, registration results derived from a historical series of localization images (e.g., from different treatment sessions) may be reviewed as a sequence. This analysis may involve quantifying parameters such as systematic and random geometric setup errors (e.g., when the patient is not exactly in the same position in different treatment sessions) and/or anatomical changes within the patient (e.g., breathing motion, a filled bladder, a filled rectum, and the like). According to the outcome, the review may be used to trigger various downstream changes in the patient's treatment (e.g., modified setup instructions and/or adaptation of the prescription for subsequent treatment sessions).

In some embodiments, the radiation therapy system may include a Graphical Use Interface (GUI) to streamline the process of reviewing 3D patient images, 2D stereo pairs, and/or individual 2D images. The GUI may provide an efficient mechanism to visually compare images across a plurality of treatment days, making it easier to identify unusual image features that may require further investigation. The GUI may also allow displaying changes in spatial information over time with the image data, such as changes in offset values. The GUI may include limited floating windows that open and close, so that the user does not need to continually adjust to changing visual information. For example, the GUI may remove or decrease the discontinuity within the review of a workflow, such as when a user has to start, stop, or restart a various application or elements within the software. The discontinuity typically occurs when a user has to switch his/her attention to different patients or when a user has to switch attention between an image and graphical trend information.

FIG. 1 illustrates an exemplary image work list depicting images needing review by a particular staff member (e.g., a physician or a healthcare worker). In FIG. 1, table 100 displays data from a database. The data are related to images in need of review by the currently logged-in staff member (e.g., a user). Table 100 includes a set of columns with data taken from the database. The columns include information about the patient from whom the images were acquired (e.g., 102), the date and time of acquisition of the image (e.g., 104), the treatment site being treated at the time the images were acquired (e.g., 106), and the acquisition modality of the images (e.g., 108). The columns also include information about the geometry of the image at the time it was acquired and the offset that was generated at the time the image was acquired (e.g., 110). The columns further include metadata about the images, such as comments and notes added during a physician's review of the images, information about the approval status of the image, and change orders resulting from the review of the images. The columns can be re-ordered, hidden, and resized to allow the user to organize the columns, in order to better interpret the text-based data contained in table 100. The rows in table 100 can be grouped according to any of the available columns, including: grouping by the patient from whom the images were acquired, grouping by the treatment site being treated at the time the images were acquired, grouping by the acquisition modality of the images, grouping by the availability of offset data or other geometric information describing the images, grouping by metadata about the images including the approval status and available comments and notes associated with the image, etc. To group the rows according to data contained in the columns, the user may click on the header (e.g., 112) of a particular column according to which the rows are to be grouped. When the rows are grouped, the grouping headers (e.g., 114) allow the collection of grouped rows to be expanded and collapsed. Each grouping header includes summary information about the collection of rows within the group, including, for example, the count of rows within the group (e.g., image count) and statistics about columns within the group such as oldest image acquisition date and time. Selection of a particular row in table 100 makes the image represented by the row available to be loaded for review.

FIG. 2 illustrates an exemplary image list for a particular patient. In FIG. 2, table 200 includes a set of columns with data taken from the database. The columns can be re-ordered, hidden, and resized to allow the user to organize the columns, so as to be able to better interpret the text data contained in table 200. The columns include, for example, the date and time of acquisition of the image (e.g., 202), the treatment site being treated at the time the images were acquired (e.g., 204), and the acquisition modality of the images (e.g., 206). The columns also include information about the geometry of the image at the time it was acquired, and the offset that was generated at the time the image was acquired (e.g., 208). The columns also include metadata about the images, such as the current approval status and change orders resulting from review of the images, and any comments or notes that were recorded at the time of review of the images.

The rows within table 200 can be grouped by any of the available columns, including grouping by the treatment site being treated at the time the images were acquired, grouping by the acquisition modality of the images, grouping by the availability of offset data or other geometric information describing the images, grouping by metadata about the images including the approval status and available comments and notes associated with the image. For example, the user may click the column header according to which the data is to be grouped to sort the rows in table 200. After grouping the rows, the grouping headers allow the collection of grouped rows to be expanded and collapsed, and each grouping header includes summary information about the collection of rows within the group, including the count of rows within the group and statistics about columns within the group such as oldest image acquisition date and time.

Table 200 includes buttons for performing various operations on the images, including opening the image (e.g., button "Open"), reviewing the image (e.g., button "Review"), deleting the image (e.g., button "Delete"), updating the data display for new images that may have been received (e.g., button "Refresh"), and examining auxiliary data objects associated to the image (e.g., button "SRO Browser"). The buttons operate on individual image rows, which can be selected for operations provided by the buttons.

FIG. 3 illustrates an exemplary trend table 300 depicting numerical offset values for a particular patient. Trend table 300 includes information about the treatment site for which offsets have been calculated (e.g., 302), as well as the patient geometry at the time of treatment (e.g., 304). Trend table 300 includes a row for each of the offsets that have been calculated for a particular image, and the rows are grouped by treatment site. The grouping can be expanded or collapsed, so the user can adjust the amount of detail displayed on trend table 300. Trend table 300 includes columns for the description of each of the offset entries (e.g., 306), the date and time of the image to which each offset is associated (e.g., 308), the superior, lateral, and anterior components of the offset and the direction of each of these (e.g., 310), the sagittal, coronal, and transverse rotational components of the offset (e.g., 312), and the total magnitude of the translation part of the offset (e.g., 314). Trend table 300 also includes inputs for modifying the existing patient setup as a result of observations made from the tabular display of offset data on trend table 300 (e.g., through input section 316). A button (e.g., 318) is also provided to access the trend graph, which is an alternative graphical chart for displaying offset trends.

While the tabular display format provides flexibility for formatting and displaying textual data, it falls short of providing an effective mechanism for interpreting changes in image data. The following embodiments provide more efficient ways for visually detect relevant changes in the image data that have not been explicitly represented as textual data.

FIG. 4 illustrates an exemplary graphical representation of offset trends. In FIG. 4, trend graph 400 includes information (e.g., 402) about the treatment site for which the offsets have been calculated, as well as the patient geometry at the time of treatment. Trend graph 400 includes multiple subgraphs (e.g., 404, 406, 408), depicting each of the different components of the offset. The components of the offset that are depicted include the superior, lateral, and anterior translation components (shown in the front tab "Planar Graphs"), as well as sagittal, coronal, and transverse rotational components (hidden in the background tab "Rotational Graphs"). On each subgraph, the numerical component of the offset is charted as a function of time. The time axis of the trend graph displays the entire range of treatment days, and each component of the offset for each treatment day is depicted as a single point on the graph. Each point indicating a component of the offset for each treatment day can also display a tooltip (e.g., 414) indicating further information about the offset, including the numerical values of the offset, when the offset was modified, and/or the staff member responsible for the modification. The successive components of the offset are connected by line segment to aid in the visual assessment of how the offset changes over time. Trend graph 400 also includes inputs (e.g., through input box 416) for modifying the existing patient setup based on the data contained in the trend graph, making use of known protocols including the Shrinking Action Level (SAL) protocol and/or the No Action Level (NAL) protocol.

Figure 5:
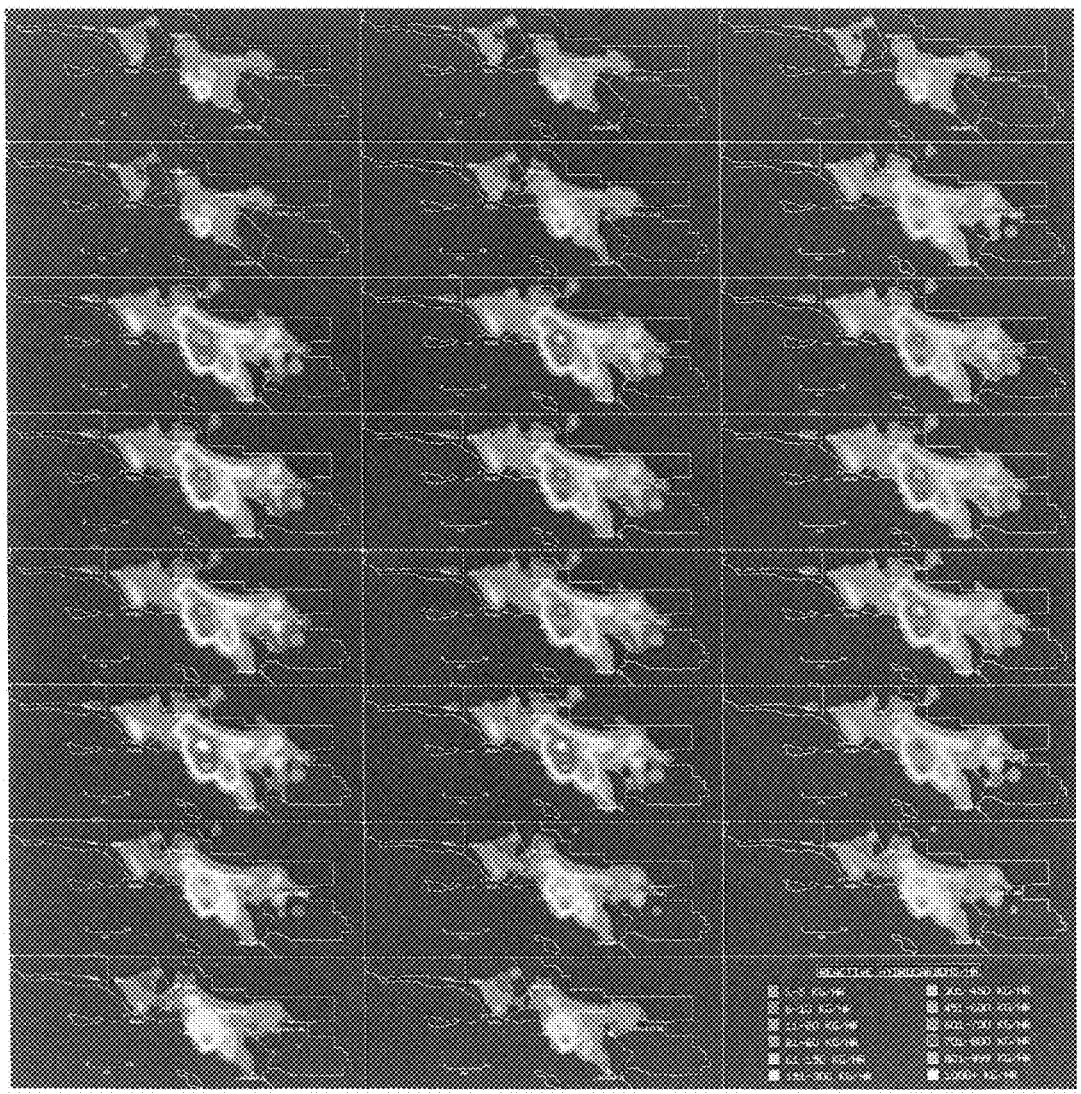
FIG. 5 illustrates an image interface using small multiples, according to some embodiments of the present disclosure.

FIG. 5 illustrates an image interface using "small multiples", an efficient data visualization technique for interpreting and comparing complex data. The static composition of small multiples into a grid layout is challenging when the individual graphics are medical images because medical images contain large amounts of data, and generally require interactive manipulation in order to fully extract and interpret meaning from the images. For example, many of the features of interest in a CBCT are small relative to the size of the entire CBCT image (e.g., a prostate within a pelvic scan), which would be difficult to view in a thumbnail-sized image. However, interactions with the plurality of medical images require significantly more screen space than would be afforded by each of the individual graphics within the grid of small multiples. One advantage of using small multiples with high density data is that small multiples technique facilitates the visual comparison of a plurality of features across multiple images. Examining a single image at a time in a large viewer may not reveal all the relevant features because some of the features of interest may only be appreciated as changes over time. For example, changes in the shape or density of a tumor or an adjacent organ at risk are preferably analyzed with respect to changes over time.

Figure 6A:
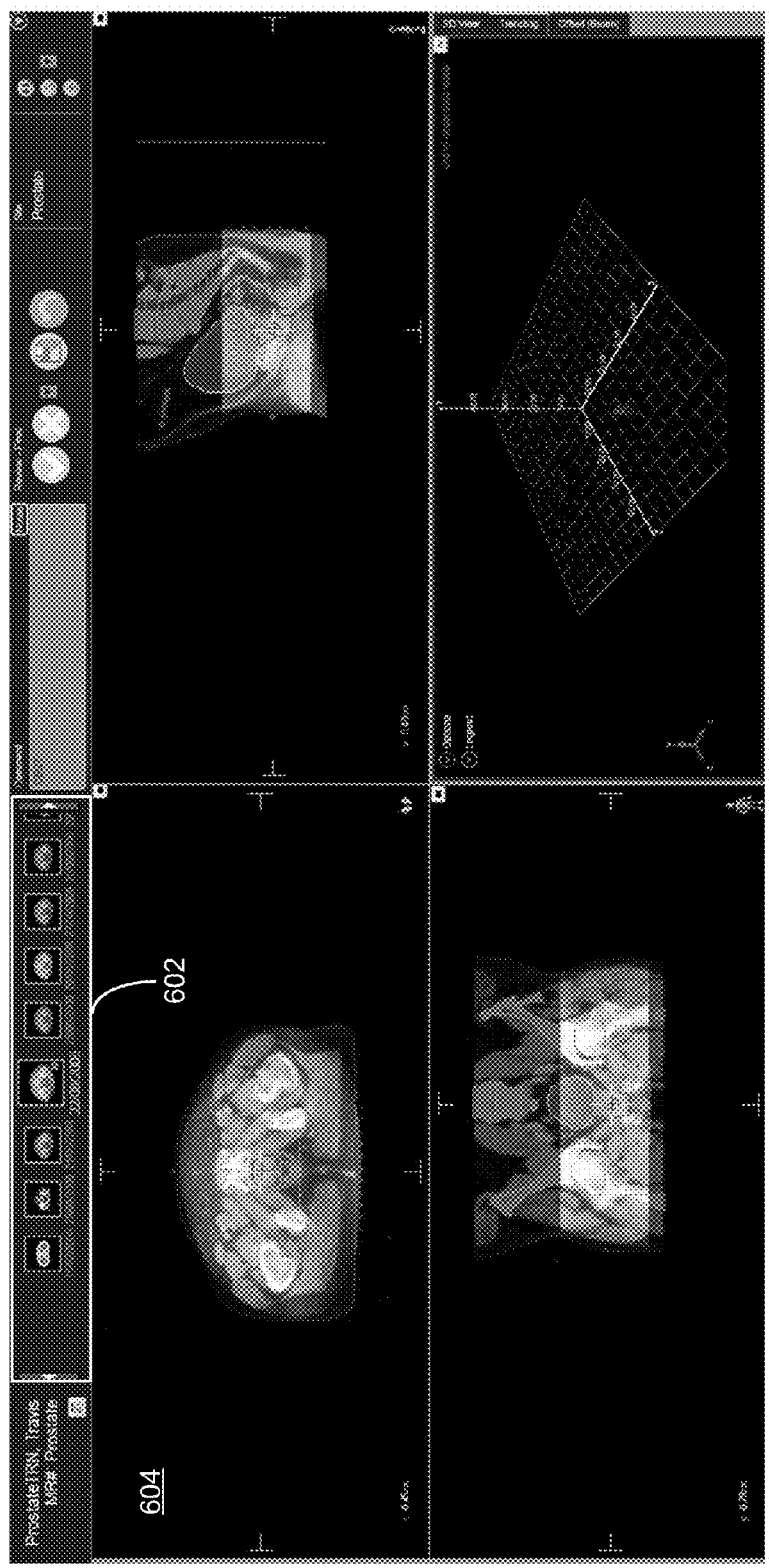
FIG. 6A illustrates an exemplary user interface with a patient timeline carousel, according to some embodiments of the present disclosure.

FIG. 6A illustrates an exemplary user interface with a patient timeline carousel. In FIG. 6A, carousel 602 includes a grid display of a plurality of thumbnail images. Carousel 602 allows one of the thumbnail images in the grid to be selected and highlighted (e.g., placed in a "front position"), and simultaneously allow viewing and interaction of the particular selected image in an adjacent larger viewer, such as main viewer 604 (or any other viewer that a user may select). For example, upon selection of a particular thumbnail image, the image associated with the thumbnail is retrieved from memory and displayed in main viewer 604.

The interaction may be further enhanced using an animation effect to scroll (e.g., rotate carousel 602 either left or right) as the user selection changes. The resulting carousel display brings the advantages of small multiples presentation of images. This allows a user (e.g., a physician) to review medical images of various kinds, such as one or more CT images, MRI images, x-ray images, radiotherapy portal images, stereo pairs of portal images, stereo pairs of x-ray images, PET images, SPECT images, ultrasound images, and any combination thereof.

As the user interacts with the image corresponding to the selected thumbnail image from carousel 600 in main viewer 604, the user interactions such as adjusting the window/level of one or more images, changing the zooming or panning level of the images, or changing the slice orientation or slice position parameters of the image may also be applied to the thumbnail images in carousel 600. This allows for an enhanced comparison of the plurality of thumbnail images loaded in carousel 600. Images acquired throughout the course of an IGRT treatment typically have the same acquisition parameters, so the same window/level, zoom, pan, slice orientation and slice position parameters can apply to all of the images displayed within carousel 600. The resulting aggregation allows for expedient identification of unusual trends within the images or anomalies within individual images.

The thumbnails within carousel 600 may be augmented with visual indicators of metadata associated with the image. Metadata may include image status, change orders, image acquisition date and time, image modality, other acquisition parameters (e.g., energy used, filters used), image geometry, offset values, treatment site, comments, notes, and the like. Image status information, such as image approval or rejection, may be depicted with colored borders. Tooltips may also be available with more detailed information for each image and may include, for example, image comments, notes, and offset numerical values.

Figure 6B:
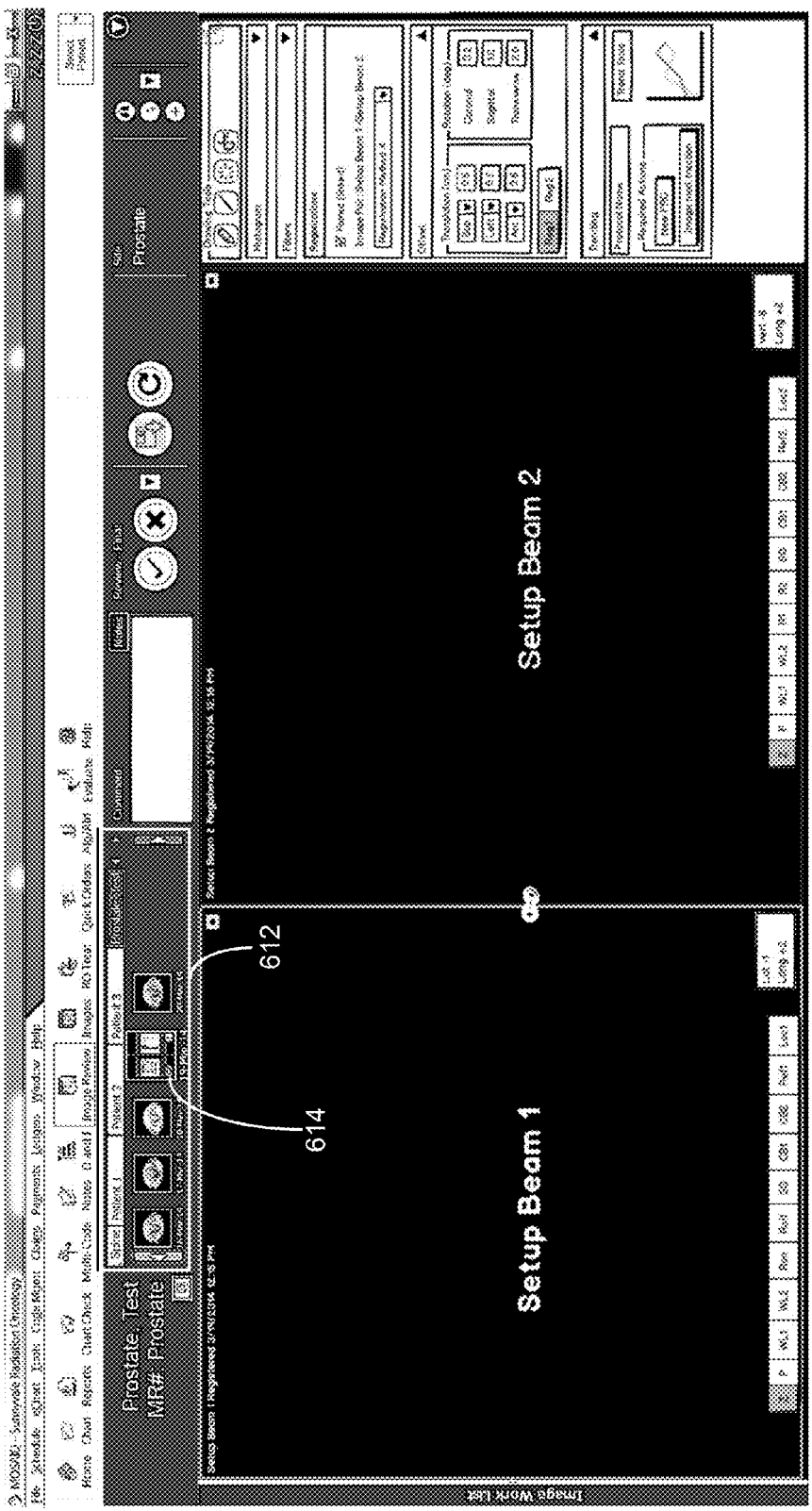
FIG. 6B illustrates another exemplary patient timeline carousel, according to some embodiments of the present disclosure.

FIG. 6B illustrates another exemplary patient timeline carousel 612 depicting a single pair of stereo portal images, where two individual images are adjoined into a single thumbnail. An additional icon (e.g., 614) represents that link is formed between the two portal images comprising the stereo pair. Upon selection of the stereo pair thumbnail, both portal images and their respective reference images may be displayed in a single layout that can be used to visualize a single 3-dimensional offset value derived from the relative alignment of both portal images.

Figure 7:
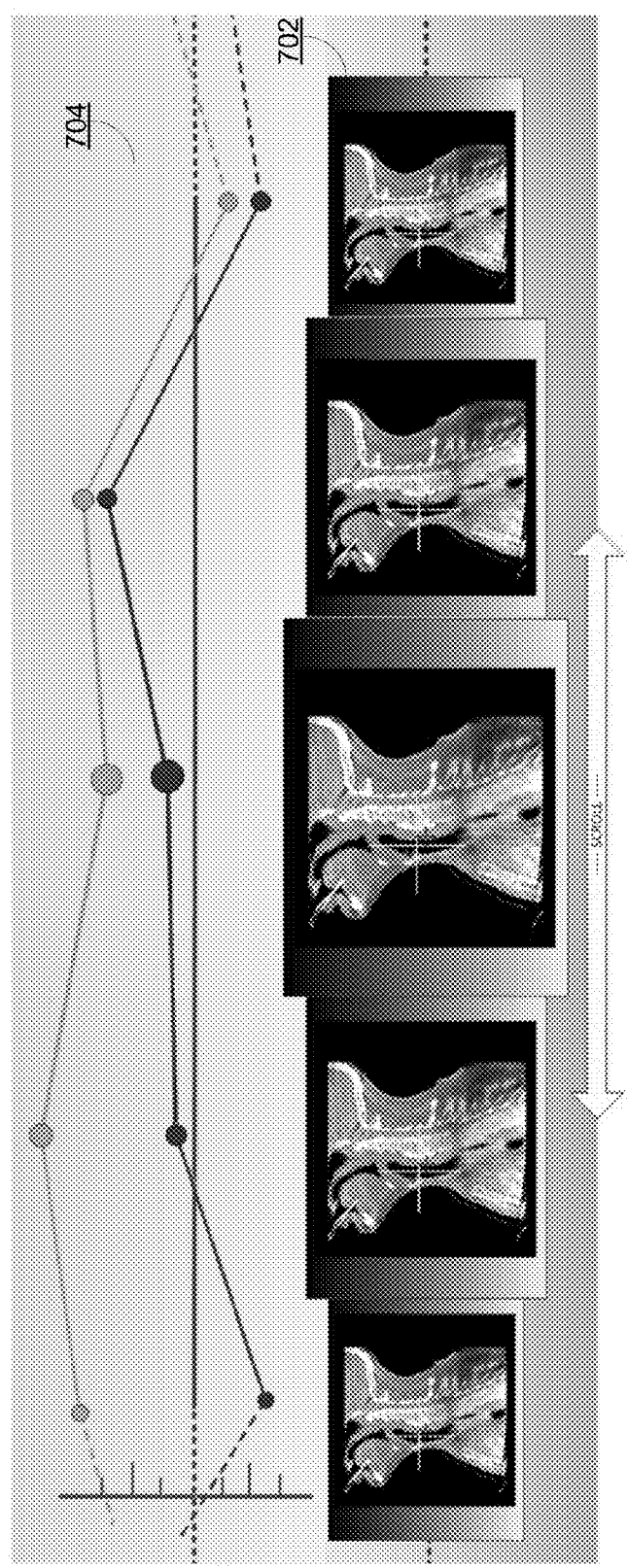
FIG. 7 illustrates an exemplary integrated trend graph, according to some embodiments of the present disclosure.

FIG. 7 illustrates an exemplary integrated trend graph. As shown in FIG. 7, the display of a carousel 702 may be synchronized to a trend graph 704 for offset values. This allows the physician easy identification of images for which the offset is outside the range of expected bounds. In some embodiments, trend graph 704 may be populated from daily offsets from each of the daily images of the patient. Trend graph 704 may be linked to the images loaded in the scrolling carousel 702, so that trend graph 704 flows forwards and backwards corresponding to the respective daily thumbnail images displayed in carousel 702. Linking trend graph 704 and carousel 702 is advantageous for a physician when browsing or reviewing a selected patient's IGRT history because trend graph 704 provides a relevant clinical context (e.g., what caused the particularly large offset yesterday or which was the day last week when we saw that large shift) for the plurality of thumbnail images to the physician when selecting a particular thumbnail image to be loaded in the main viewer. In addition, other parameters may be highlighted on trend graph 704. For example, translations, rotations, action points from a Shrinking Action Level (SAL) or No Action Level (NAL) protocol, biological metrics such as Effective Uniform Dose (EUD), Tumor Control Probability (TCP) and Normal Tissue Complication Probability (NTCP), and the like may be displayed. Therefore, the integrated trend graph shown in FIG. 7 provides an efficient and useful means for browsing an overview of IGRT image-sequential highlights.

Figure 8:
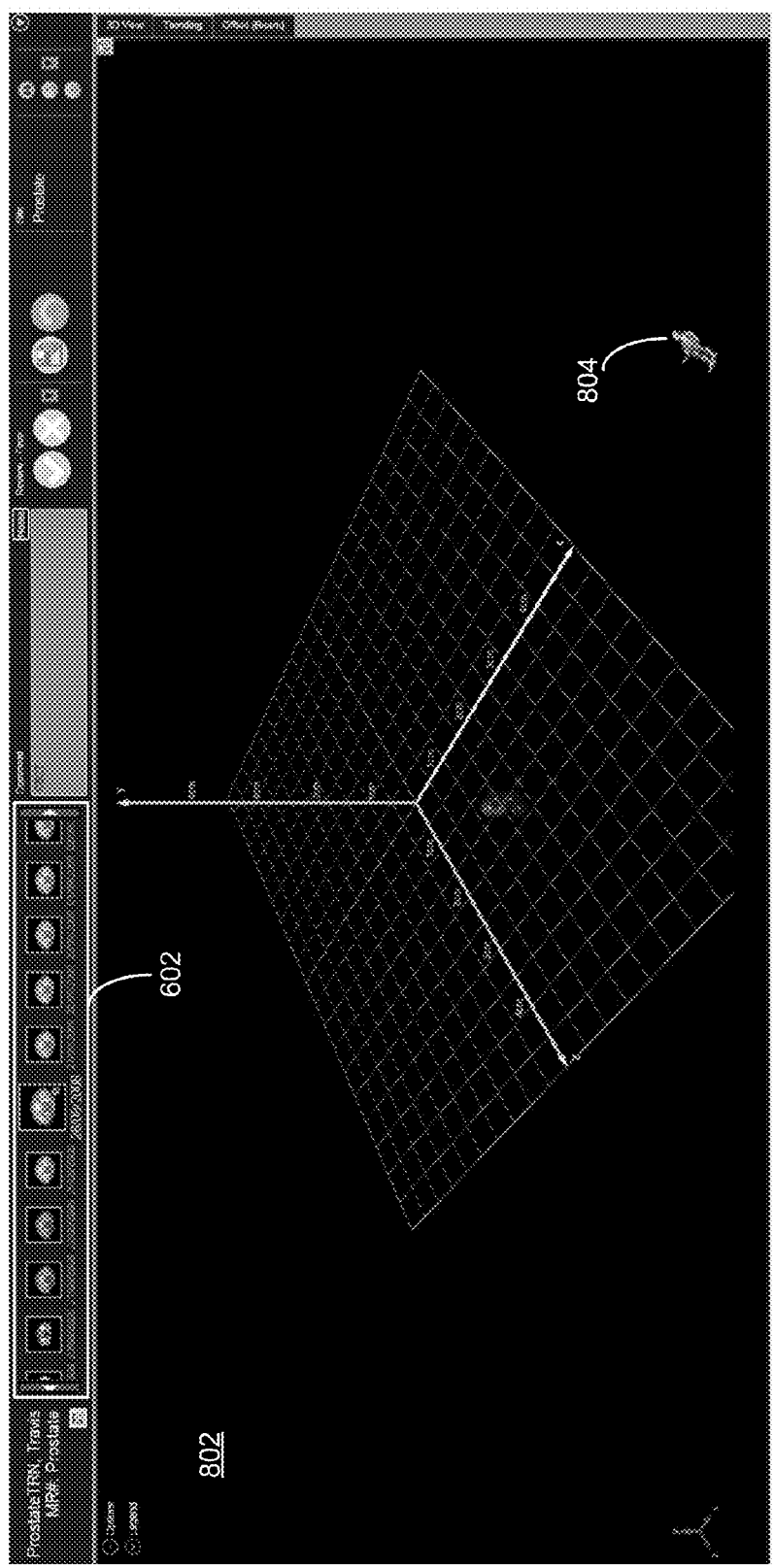
FIG. 8 illustrates an exemplary scatter plot diagram, according to some embodiments of the present disclosure.

FIG. 8 illustrates an exemplary scatter plot diagram. In FIG. 8, offset values for the three axes in a single 3-dimensional scatter plot are displayed. The scatter plot uses colors (e.g., green and blue as shown in FIG. 8) and filters to represent the offsets belonging to certain time periods (e.g., in one embodiment grouped by week). Spatial scale is displayed in the scatter plot using axis hash marks (e.g., in one embodiment at 1 cm and 5 cm), and orientation is displayed using axis labels and an anatomical icon (e.g., icon 804). A user may then select an individual offset value and the corresponding thumbnail image and image stored in the memory will be selected and provided for display in main viewer 802.

In one embodiment, a user may zoom, pan, and rotate the scatter plot to acquire a better 3D view of the relationship between offset values. As the viewing orientation of the scatter plot is adjusted, the presentation of the anatomical icon 804 (e.g. in the form of a digital mannequin) may also be updated to reflect the current viewing direction in terms of easily recognizable patient anatomical axes. In addition, the user may enable and disable particular offset values that correspond to particular periods of time. Furthermore, a tooltip may be available for each of the offset points. The tooltip may provide additional information about the offset, including, for example, a date and time of the offset, the staff member responsible for the offset, and the numerical offset values.

The individual offset values displayed in the scatter plot are selectable, and selection of an offset in the scatter plot serves the same role as selection of a thumbnail in carousel 602. Therefore, a user can move (e.g., rotate, slide, drag, and the like) carousel 602 to the left or the right to view the thumbnail images. By moving carousel 602 to the left, images earlier in time are displayed, while moving carousel 602 to the right displays images taken later in time. The selected image is shown in the front view that highlights the fact that this image has been selected to be viewed in a main viewer 802. Therefore, the image corresponding to the selected offset is displayed in main viewer 802, where it can be examined more thoroughly.

For example, a physician may explore portions of the patient image data in greater detail in main viewer 802 than what is presented in the thumbnail. Further, a physician may use the image content to assess and understand the state of the anatomy of interest at the specific time the image was acquired (generally the point of treatment) with particular interest in: (a) the geometric disposition of the anatomy with respect to the treatment machine geometry (e.g., is/was the patient correctly positioned); and (b) significant deviations in the layout of internal anatomy due to effects such as tumor shrinkage, bladder volume, rectal filling, and the like.

A more thorough examination of the image in the image viewer may include:

Navigating through the slices of the image;

Zooming and panning to navigate to specific regions within the image;

Windowing/leveling the pixel values in the image;

Applying filters to the pixel values in the image;

Switching between the two images forming a stereo pair of 2D portal images;

Examining the registration of the image with its reference image using multiple modes to co-display two images, including alpha blending, additive blending, spyglass display, checkerboard display, and quartered display;

Modifying the registration of the image with its reference image;

Examining the overlap of the images with co-displayed regions of interest;

Examining the image with overlaid isodose lines derived from the reference image;

Generating a three-dimensional volume rendering of the image; and/or

Rotating a three-dimensional volume rendering of the image.

Figure 9:
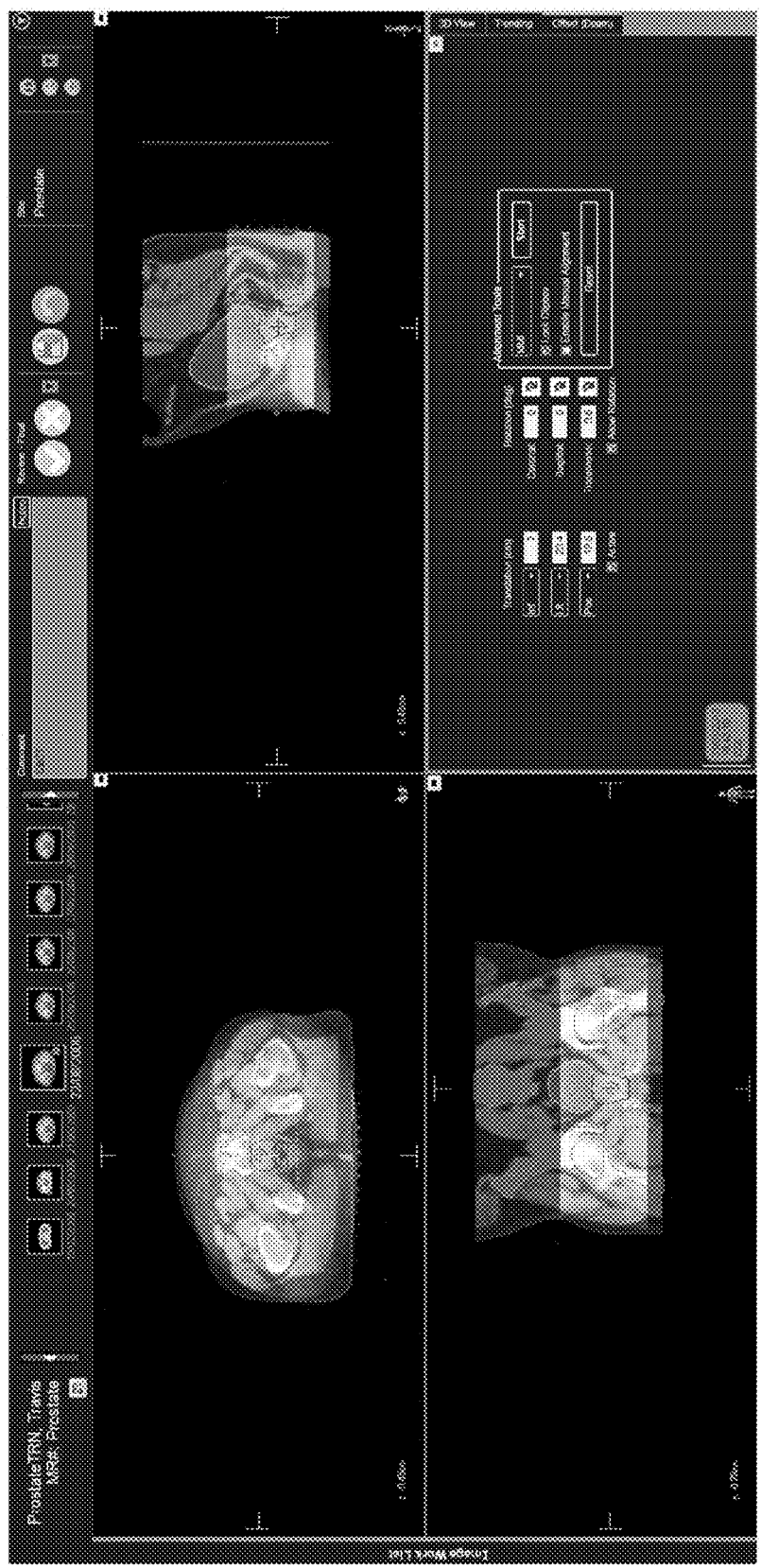
FIG. 9 illustrates an exemplary work list mode, according to some embodiments of the present disclosure.

In some embodiments, carousel 602 may include at least two modes of operation. The patient timeline mode displays images for a single patient as depicted by, for example, FIG. 6A. The work list mode displays the images needing review by the current user as depicted in, for example, FIG. 9. In FIG. 9, an input window is provided on the lower right portion to allow changing of various parameters. Additional modes of operation are permissible, such as the ability to sort thumbnail images by magnitude of offset or other extracted numerical values. Further, the user may be able to filter the thumbnail images by a time range.

Figure 10:
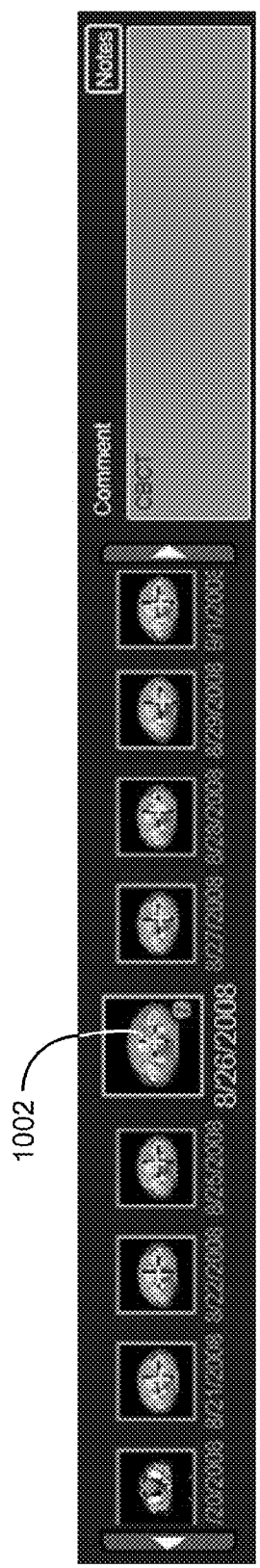
FIG. 10 illustrates an exemplary isocenter overlap, according to some embodiments of the present disclosure.

FIG. 10 illustrates an exemplary isocenter overlap, providing visualization for the thumbnails that includes the offset information directly on the thumbnails, as the relative shift between two different isocenter positions. As depicted in FIG. 10, the yellow colored cross-hairs (e.g., 1002) identify an isocenter for each particular image, which is advantageous in visualizing the offset. In an embodiment, multiple simultaneous offset values can be calculated for different regions of the image, or calculated using different characteristics of the image content such as bone, soft tissue, and the like, which are referred to as dual registration protocols. Furthermore, some of the spatial information (e.g., from the trend graph or scatter plot) may be directly displayed on the thumbnail image, where the visual context can further enhance the interpretation of the image. Moreover, FIG. 10 allows selection of the image directly from the isocenter offset instead of having the trend graph synchronized to the carousel to show the offset values for each image as shown in FIG. 7.

In some embodiments, visualization for the thumbnails may include technique in which the CBCT is co-registered to the reference image using one of a number of standard dual display modes. Additive blending of magenta and green is one of the common display modes that allows for quick identification of changes in relative registration. Although magenta and green have been described in this example, multiple other colors may be used in order to depict the contrast for providing a user quick identification of changes in the relative registration.

In another embodiment, a visualization is provided to overlay the thumbnail with additional information generated by advanced automated post-processing, such as Atlas Based Auto Segmentation (ABAS) software commercially provided by Elekta, Sweden. ABAS can produce re-segmented structures, which can be overlaid on top of the CBCT thumbnail to highlight changes that have occurred to the structures. ABAS can also produce a deformable registration vector field, and visual indications of large deformations can be overlaid on top of the thumbnail to indicate areas where further examination may be needed.

Figure 11:
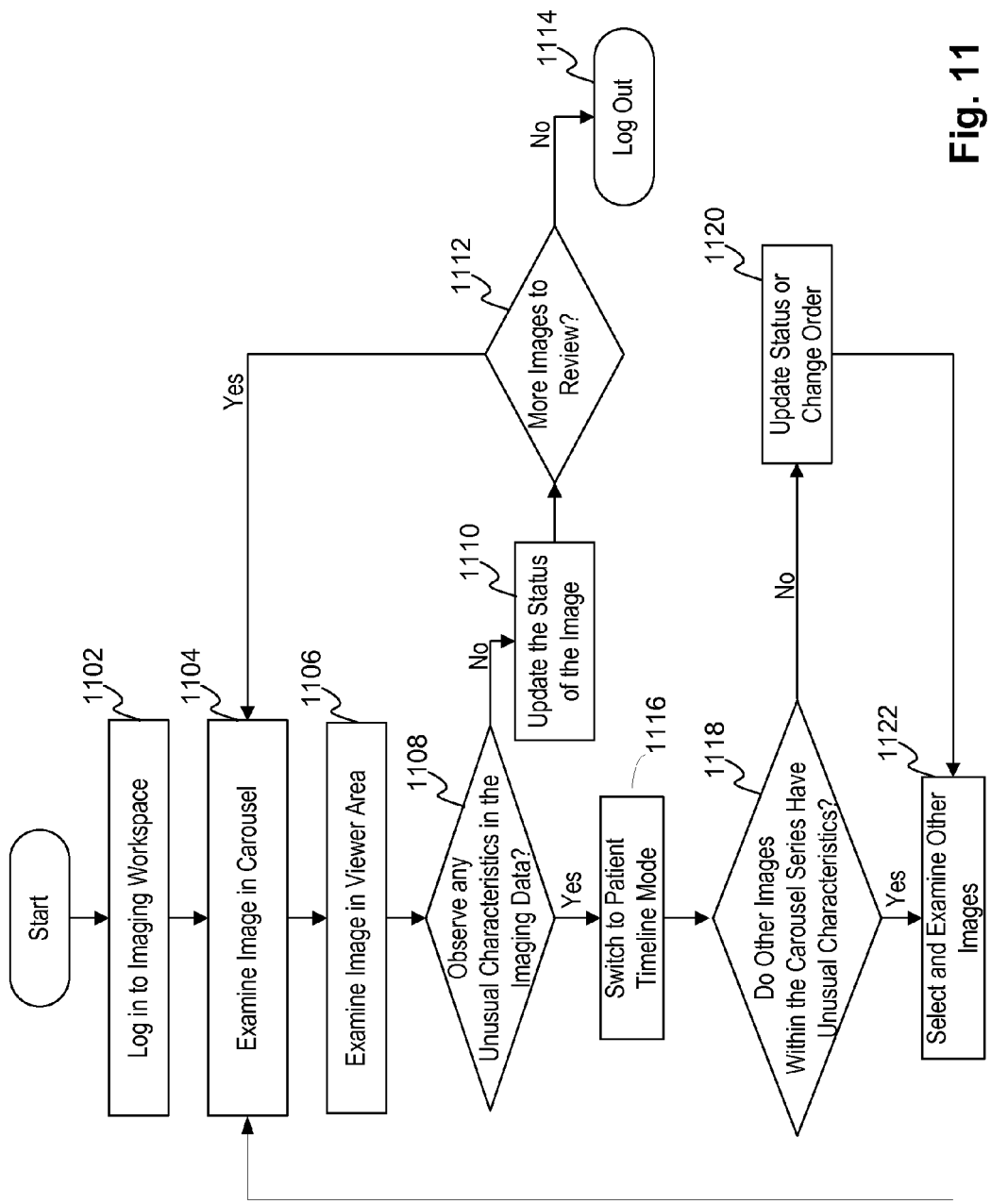
FIG. 11 is a flowchart of an exemplary workflow using an exemplary radiotherapy system.

FIG. 11 is a flowchart depicting the workflow using both the work list mode and the patient timeline mode. When in work list mode, only the thumbnail images requiring a physician's review are shown in the carousel. Images that have been previously reviewed are not shown in the carousel. Thus, this is more efficient because the physician does not have to sort through a work list of images to determine if the image has been reviewed or not because only those images not reviewed are provided in the carousel. The tasks depicted by FIG. 11 can be performed simultaneously or in a different order than that depicted.

Upon a user (e.g., a physician or a health-care worker) logging into the imaging workspace (step 1102), a group of images that are required to be reviewed, which are stored in memory, are loaded into the carousel (e.g., carousel 602). The user can then examine each image by selecting (step 1104) a particular image from the carousel which will result in the image to be presented in a larger main viewer (step 1106). Any observations of any unusual characteristics can then be determined (step 1108). The thumbnails within the carousel may be augmented with visual indicators of metadata associated with the image. Metadata may include information, such as image status information (e.g., image approval or rejection) and may include more detailed information for each image, including image comments, notes, and offset numerical values. In addition, metadata may include information relating to the origin and the credentials of the image (e.g., date and time the image was acquired, image status, change orders, image modality, specific imaging device used, settings on the machine that took the image, acquisition parameters, the amount of imaging energy used, image geometry, offset values, treatment site, identification strings such as, for example, DICQM, and unique identifiers, as well as comments, notes and the like).

The user may update the status of the image (step 1110) and then continue to review additional images (1112). If no more images need review, the user may log out (step 1114). Alternatively, the physician may switch to a patient timeline mode (step 1116) to review the images over a period of time days (e.g., 2 days, 7 days, 30 days, 90 days, and the like). The physician can determine if there are any unusual characteristics in the image data by comparing successive images taken on successive days (step 1118). If required, the physician can select one or more images to be presented in a larger main viewer for further examination. Based on this examination, the physician may order/prescribe other procedures, indicate status changes, and/or the like (step 1120). The user may select and examine other images in a similar manner (step 1122).

Figure 12:
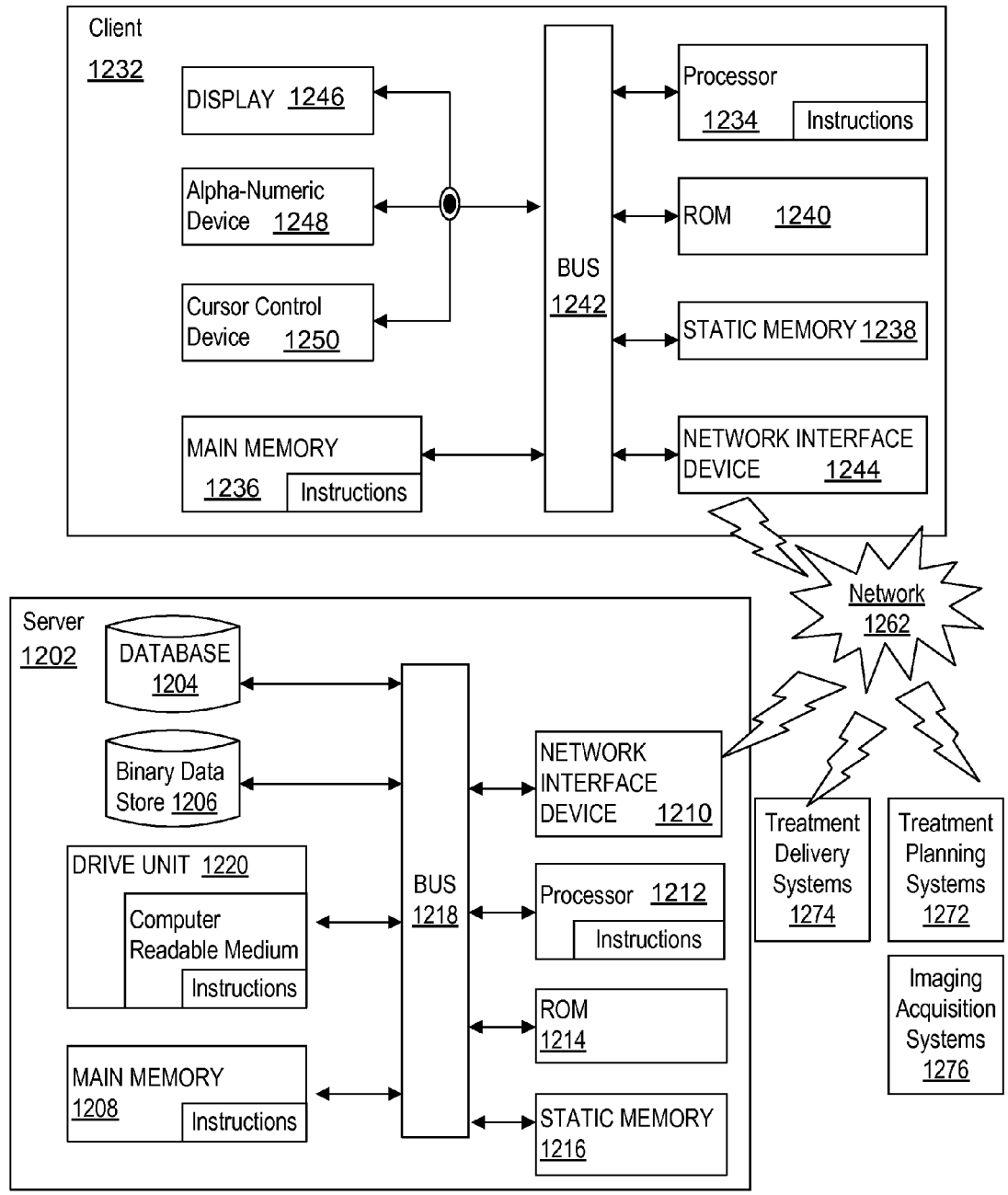
FIG. 12 illustrates an exemplary block diagram of an exemplary radiotherapy system.

FIG. 12 is an exemplary system block diagram depicting the components of a radiotherapy system (e.g., an Oncology Information System (OIS)). An OIS may include a server 1202 containing the common database and other related files representing the data for patients under treatment. An OIS may also include clients (e.g., client 1232) that are connected to the server via a network 1262. Server 1202 may include the stored program files that are used to load the software on to client 1232. Server 1202 may include a main memory 1208 in to which computer instructions are loaded, a processor 1212 to execute the instructions, and a static memory 1216 that stores data related to the currently executing program. A read-only memory (ROM) 1214 may contain computer instructions related to starting the server and to the operation of hardware devices attached to the server. A system bus 1218 may convey data between the components that make up the server. A drive unit 1220 attached to server 1202 may contain computer instructions for various software programs that make up the OIS. These instructions may be loaded when the user requires them to execute functionality of the OIS, or when system events occur that require responses. A database 1204 may be attached to and managed by server 1202, which acts as the central repository of data stored and managed by the OIS. A Binary Data Store 1206 may also be attached to server 1202, which stores additional large pieces of data that are not conveniently stored in the database, such as images from an Image Acquisition system. Server 1202 may include a Network Interface Device 1210 that allows it to communicate to other nodes on the network, including OIS clients (e.g., client 1232), Imaging Acquisition Systems (e.g., 1276), Treatment Planning Systems (e.g., 1272), and Treatment Delivery Systems (e.g., 1274).

Client 1232 may include a processor 1234, main memory 1236, static memory 1238, and ROM 1240, as well as a system bus 1242 that conveys data among the components of client 1232. Client 1232 may include a Network Interface Device 1244 through which it communicates to server 1202. Client 1232 may load its software over network 1262, from instructions stored on the Drive Unit 1220 of server 1202. Client 1232 may include components that are utilized by the user interface of the OIS, including a display device 1246 such as an LCD screen, an alpha-numeric entry device 1248 such as a keyboard, and a cursor control device 1250 such as a mouse. Data that displayed by client 1232 may be requested from server 1202 over network 1262, and changes to data made by client 1232 may be conveyed to server 1202 to be stored in database 1204 or in the Binary Data Store 1206. Multiple clients can be connected to a single server, and multiple Treatment Delivery systems, Image Acquisition systems, and Treatment Planning systems may also be connected to a single server.

In some embodiments, the radiation therapy system may be connected (e.g., networked) to other machines in a Local Area Network (LAN), an intranet, an extranet, or the Internet. One or more machines of the radiation therapy system may operate in the capacity of a server or a client machine in a client-server network environment, or as a peer machine in a peer-to-peer (or distributed) network environment. The machine may be a personal computer (PC), a tablet (e.g., an iPad, a Microsoft Surface tablet, and the like), a Personal Digital Assistant (PDA), a cellular telephone (e.g., an iPhone, and the like), or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein. In some embodiments, a central server and multiple parallel workstations maybe connected via a network.

In some embodiments, new images of the patient may arrive to the radiation therapy system in real-time. The new images provided in real-time may be loaded onto the carousel in real-time. Further, the carousel may visually indicate the arrival of these new images for the physician or the healthcare worker, and may further indicate that these new images need to be reviewed.

The radiation therapy system may include a processor, a main memory, a read-only memory (ROM), a flash memory, a dynamic random access memory (DRAM) such as synchronous DRAM (SDRAM) or Rambus DRAM (RDRAM and the like), a static memory (e.g., flash memory, static random access memory (SRAM and the like)), and may include a secondary memory (e.g., a data storage device such as a memory cache), which communicates with the processor and static and main memory via a bus. In accordance with some embodiments, main memory stores computer-executable instructions corresponding to a plurality of tasks. These computer-executable instructions may be executed by the processor. Further, cached memory may be pre-formatted to increase the speed for faster loading of data.

In some embodiments, the memory may be a machine readable storage medium. While the machine-readable storage medium as an exemplary embodiment may be a single medium, the term "machine-readable storage medium" should be taken to include a single medium or multiple media (e. g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present invention. The term "machine readable storage medium" shall accordingly be taken to include, but not be limited to, solid-state memories, and optical and magnetic media.

The processor represents one or more general-purpose processing devices such as a microprocessor, central processing unit, or the like. More particularly, the processor may be a complex instruction set computing (CISC) microprocessor, reduced instruction set computing (RISC) microprocessor, very long instruction Word (VLIW) microprocessor, a processor implementing other instruction sets, or processors implementing a combination of instruction sets. Processor may also be one or more special-purpose processing devices such as an application specific integrated circuit (ASIC), a field programmable gate array (FPGA), a digital signal processor (DSP), netWork processor, a System on a Chip (SoC), or the like. As will be appreciated by those skilled in the art, in some embodiments, the processor may be a special-purpose processor, rather than a general-purpose processor.

The radiation therapy system may include a user interface device, a video display (e.g., a liquid crystal display (LCD) or a cathode ray tube (CRT)), an alphanumeric input device (e.g., a keyboard), and a cursor control device (e.g., a mouse). In an embodiment, the video display may be a screen that can be part of a hand-held communication device, such as a tablet (e.g., an iPad, an Android pad, a Nook, a reading pad, and the like), an emailing device (e.g., a Blackberry), or a cellular phone (e.g., an iPhone, a droid, and the like).

Various operations or functions are described herein, which may be implemented or defined as software code or instructions. Such content may be directly executable ("object" or "executable" form), source code, or difference code ("delta" or "patch" code). Software implementations of the embodiments described herein may be provided via an article of manufacture with the code or instructions stored thereon, or via a method of operating a communication interface to send data via the communication interface. A machine or computer readable storage medium may cause a machine to perform the functions or operations described, and includes any mechanism that stores information in a form accessible by a machine (e.g., computing device, electronic system, and the like), such as recordable/nonrecordable media (e.g., read only memory (ROM), random access memory (RAM), magnetic disk storage media, optical storage media, flash memory devices, and the like). A communication interface includes any mechanism that interfaces to any of a hardwired, wireless, optical, and the like, medium to communicate to another device, such as a memory bus interface, a processor bus interface, an Internet connection, a disk controller, and the like. The communication interface can be configured by providing configuration parameters and/or sending signals to prepare the communication interface to provide a data signal describing the software content. The communication interface can be accessed via one or more commands or signals sent to the communication interface.

The present invention also relates to a system for performing the operations herein. This system may be specially constructed for the required purposes, or it may comprise a general purpose computer selectively activated or reconfigured by a computer program stored in the computer. Such a computer program may be stored in a computer readable storage medium, such as, but not limited to, any type of disk including floppy disks, optical disks, CDROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

Embodiments of the invention may be implemented with computer-executable instructions. The computer-executable instructions may be organized into one or more computer-executable components or modules. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described herein.

When introducing elements of aspects of the invention or the embodiments thereof, the articles "a," "an," "the," and "said" are intended to mean that there are one or more of the elements. The terms "comprising," "including," and "having" are intended to be inclusive and mean that there may be additional elements other than the listed elements.

Having described aspects of the invention in detail, it will be apparent that modifications and variations are possible without departing from the scope of aspects of the invention as defined in the appended claims. As various changes could be made in the above constructions, products, and methods without departing from the scope of aspects of the invention, it is intended that all matter contained in the above description and shown in the accompanying drawings shall be interpreted as illustrative and not in a limiting sense.

What is claimed is:

1. A radiotherapy apparatus, comprising:
  a memory for storing a plurality of images; and
  a processor communicatively coupled to the memory, wherein the processor is configured to execute instructions for:
    providing a carousel to display thumbnail images corresponding to the plurality of images to a user;
    receiving an input from the user for selecting at least one thumbnail image displayed in the carousel;
    generating a graphical user interface configured for displaying to the user at least one image stored in the memory corresponding to the at least one thumbnail image selected from the carousel; and
    generating a trend chart to display the graphical user interface, wherein a point on the trend chart is linked to a corresponding thumbnail image in the carousel,
  wherein the thumbnail images displayed in the carousel are in chronological order.

2. The radiotherapy apparatus of claim 1, wherein the plurality of images comprise at least one of: an Magnetic Resonance Imaging (MRI) image, a Computed Tomography (CT) image, an x-ray image, a radiotherapy portal image, a stereo pair of portal images, a stereo pair of x-ray images, a Positron Emission Tomography (PET) image, a Single-Photon Emission Computed Tomography (SPECT) image, and an ultrasound image.

3. The radiotherapy apparatus of claim 1, wherein the carousel rotates from left to right or from right to left.

4. The radiotherapy apparatus of claim 1, wherein the user selection of a particular thumbnail image displayed in the carousel results in a corresponding image being displayed in a main viewer.

5. The radiotherapy apparatus of claim 1, wherein the processor is configured to execute instructions for:
  creating a scatter plot including one or more offsets;
  receiving a user input for selecting a particular offset in the scatter plot; and
  displaying an image stored in the memory corresponding to the selected particular offset.

6. The radiotherapy apparatus of claim 5, wherein the scatter plot is supplemented with a mannequin icon indicating anatomical axes of a patient, and visual presentation of the mannequin is updated to reflect a current viewing orientation of the scatter plot data relative to the patient when the user selects a particular viewing direction for the scatter plot.

7. The radiotherapy apparatus of claim 1, wherein the graphical user interface comprises at least one of a cellular phone interface, a tablet interface, and a touch screen interface of a handheld device.

8. A method for treating a patient with a radiotherapy device, comprising:
  storing a plurality of images of one or more patients in a memory;
  selecting a group of images from the stored plurality of images stored in the memory;
  loading a carousel with thumbnail images of the selected group of images;
  displaying the thumbnail images in chronological order in the carousel;
  receiving a user selection of at least one thumbnail image from the carousel;
  correlating the selection of the thumbnail image to a corresponding image stored in the memory;
  displaying the corresponding image stored in the memory on a user selected area in a graphical user interface; and
  generating a trend chart to display in the graphical user interface, wherein a point on the trend chart is linked to a corresponding thumbnail image in the carousel.

9. The method of claim 8, further comprising rotating the thumbnail images in the carousel, wherein the carousel rotates from left to right or rotates from right to left.

10. The method of claim 8, further comprising arranging the thumbnail images according to treatment time.

11. The method of claim 8, wherein the plurality of images comprise at least one of: an Magnetic Resonance Imaging (MRI) image, a Computed Tomography (CT) image, an x-ray image, a radiotherapy portal image, a stereo pair of portal images, a stereo pair of x-ray images, a Positron Emission Tomography (PET) image, a Single-Photon Emission Computed Tomography (SPECT) image, or an ultrasound image.

12. The method of claim 8, wherein the selected group of images are selected based on at least one parameter, wherein the at least one parameter includes at least one of: a particular patient; a particular organ; a particular date; a particular range of dates; or a particular disease.

13. The method of claim 8, further comprising
receiving a request from the user to group the plurality of images stored in the memory, wherein the request includes at least one of a keyboard command, a GUI toolbar item selection, or a movement or gesture created with a pointing device.

14. A method for treating a patient with a radiotherapy device, comprising:
storing a plurality of images of one or more patients in a memory;
selecting a group of images from the stored plurality of images stored in the memory;
loading a carousel with thumbnail images of the selected group of images;
displaying the thumbnails images in chronological order in the carousel;
receiving a user selection of at least one thumbnail image from the carousel;
correlating the selection of the thumbnail image to a corresponding image stored in the memory;
displaying the correlated image stored in the memory on a user selected area in a user-interface; and
creating a trend chart, wherein the trend chart comprises at least one of:
a plurality of Superior/Inferior offset values;
a plurality of Left/Right offset values; or
a plurality of Anterior/Posterior offset values.

15. The method of claim 14, wherein each offset value is based on a particular image of the patient.

16. The method of claim 8, further comprising,
receiving a user input for selecting a particular thumbnail image in the carousel; and
placing the selected thumbnail image in a front position of the carousel.

17. The radiotherapy apparatus of claim 1, wherein the thumbnail images are augmented with visual indicators of metadata associated with the thumbnail images.

* * * * *

UNITED STATES PATENT AND TRADEMARK OFFICE
CERTIFICATE OF CORRECTION

PATENT NO. : 9,539,441 B2  
APPLICATION NO. : 14/275837  
DATED : January 10, 2017  
INVENTOR(S) : Derek Graham Lane and Andrew Philip Long Page 1 of 1

It is certified that error appears in the above-identified patent and that said Letters Patent is hereby corrected as shown below:

In the Claims

Claim 1, Column 14, Line 12, "generating a trend chart to display the graphical user" should read --generating a trend chart to display in the graphical user--.

Signed and Sealed this  
Eleventh Day of April, 2017

Michelle K. Lee  
*Director of the United States Patent and Trademark Office*